United States Patent [19]

Bergfeld et al.

[11] 4,316,031
[45] Feb. 16, 1982

[54] PROCESS FOR THE PREPARATION OF 2-MERCAPTOBENZOTHIAZOLE

[75] Inventors: Manfred Bergfeld, Erlenback; Hans-Georg Zengel, Kleinwallstadt; Heinz Praetorius, Duren-Lendersdorf, all of Fed. Rep. of Germany

[73] Assignee: Akzona Incorporated, Asheville, N.C.

[21] Appl. No.: 23,986

[22] Filed: Mar. 26, 1979

[30] Foreign Application Priority Data

Apr. 15, 1978 [DE] Fed. Rep. of Germany ....... 2816407

[51] Int. Cl.$^3$ .......................................... C07D 277/72
[52] U.S. Cl. .................................. 546/175; 546/176; 564/416; 568/949
[58] Field of Search ................ 260/306; 548/175, 176; 560/949; 564/416

[56] References Cited

U.S. PATENT DOCUMENTS

| | | | |
|---|---|---|---|
| 1,631,871 | 6/1927 | Kelly | 548/176 |
| 1,785,656 | 12/1930 | Sebrell et al. | 548/175 |
| 2,001,587 | 5/1935 | Semon et al. | 548/176 |
| 2,247,894 | 7/1941 | Smith | 260/306 |
| 3,142,705 | 7/1964 | Freytag et al. | 568/949 |

FOREIGN PATENT DOCUMENTS

| | | | |
|---|---|---|---|
| 583086 | 5/1954 | Canada | 260/306 |
| 173545 | 1/1922 | United Kingdom | 564/416 |
| 179306 | 8/1964 | U.S.S.R. | 260/306 |
| 237861 | 11/1969 | U.S.S.R. | 568/949 |

*Primary Examiner*—Donald G. Daus
*Assistant Examiner*—D. B. Springer
*Attorney, Agent, or Firm*—Francis W. Young; Robert F. Green

[57] ABSTRACT

A process for the preparation of 2-mercaptobenzothiazole is disclosed. The process comprises heating a reaction mixture comprising nitrosobenzene, hydrogen sulfide and carbon disulfide in a molar ratio of about 1:1.5 to 4:1 to 3, respectively, to a temperature from about 200 to about 300° C., for a time sufficient to convert at least a portion of the reactants into 2-mercaptobenzothiazole. In an alternative process, there is first reacted nitrosobenzene with hydrogen sulfide in a molar ratio of about 1:1.5 to 4, at a temperature from about 20 to about 100° C. for a period of time sufficient to substantially reduce the nitrosobenzene, and subsequently reacting the resulting product mixture with from about 1 to about 3 mole equivalents of carbon disulfide per mole of originally charged nitrosobenzene, at a temperature from about 200° C. to about 300° C.

11 Claims, No Drawings

PROCESS FOR THE PREPARATION OF 2-MERCAPTOBENZOTHIAZOLE

BACKGROUND OF THE INVENTION

The present invention relates to a new process for the preparation of 2-mercaptobenzothiazole.

2-mercaptobenzothiazole was described for the first time by A. W. Hofmann in the year 1887. Today, the compound, as well as its derivatives, the so-called "mercaptos", is made in large quantities and is one of the most important vulcanization accelerators. Numerous syntheses and modes of formation are known. The most important preparation processes are based on o-nitrochlorobenzene, hydrogen sulfide and carbon disulfide, or on aniline, sulfur and carbon disulfide (Ullmann, Encyclopedia of Industrial Chemistry, 3rd edition (1960), Urban & Schwarzenberg, publishers, Munich - Berlin, vol. 12, p. 304).

According to the older, discontinuous process, o-nitrochlorobenzene is first reacted with excess sodium hydrosulfide at about 100° C. to form 2-aminothiophenol. Subsequently, the reaction mixture is cooled, mixed with excess carbon disulfide, and again heated to about 80°–90° C. After cooling, it is acidified with sulfuric acid to precipitate the desired 2-mercaptobenzothiazole and the crude product is purified via the calcium salt. In the foregoing process, the yield is about 85% of theoretical.

According to the more recent, continuous process for the industrial preparation of 2-mercaptobenzothiazole, aniline is reacted with a solution of sulfur in carbon disulfide at an elevated temperature (250°–285° C.) and under a pressure of about 150 bar. In such a process, the cyclization reaction is the step determining the velocity and it requires drastic conditions and the use of catalysis (e.g. phosphorus or mercury and iodine compounds). As a result of the reaction conditions, the resulting crude mercaptobenzothiazole is contaminated with tar-like by-products and must be purified through dissolution and subsequent precipitation with sulfuric acid. The yield of pure mercaptobenzothiazole is only about 80% of theoretical.

The concomitant use of a nitro or a nitroso compound, such as nitrobenzene, in the preparation of 2-mercaptobenzothiazole is also known. In the process described in U.S. Pat. No. 2,001,587, aniline, carbon disulfide and nitrobenzene are heated for 6 hours at 220° C. in an autoclave. The carbon disulfide reacts with the aniline to form an addition product, and the nitrobenzene is needed instead of elemental sulfur for the cyclization reaction, by which it is concurrently reduced to a nitrogen compound with a lower valency level. The reaction mixture is subsequently dissolved in sodium hydroxide, filtered, and mixed with hydrochloric or sulfuric acid, which precipitates the 2-mercaptobenzothiazole. Pursuant to the process of USSR Pat. No. 179,306 (C. A. 65, 2268 f (1966), aniline, sulfur, nitrobenzene and carbon disulfide are reacted with one another in a melt at elevated temperature and elevated pressure. In the synthesis, 2 mols of nitrobenzene are used per 5 mols of aniline but, in contrast to the process pursuant to the present invention, the nitrobenzene is not utilized as the only initial aromatic compound and cyclization component, but as an oxidizing agent. In the process, the selectivity and yield are low and the reaction times are very long.

A process for the preparation of 2-mercaptobenzothiazole has now been found, which is distinguished from prior art processes by milder reaction conditions, shorter reaction times and higher selectivities and yield.

SUMMARY OF THE INVENTION

There has now been discovered a process for the preparation of 2-mercaptobenzothiazole comprising heating a reaction mixture comprising nitrosobenzene, hydrogen sulfide and carbon disulfide in a molar ratio of about 1:1.5 to 4:1 to 3, respectively, to a temperature from about 200° to about 300° C., for a time sufficient to convert at least portion of the reactants into 2-mercaptobenzothiazole.

In an alternative process for the preparation of 2-mercaptobenzothiazole, the process comprises first reacting nitrosobenzene with hydrogen sulfide in a molar ratio of about 1:1.5 to 4, at a temperature from about 20° to about 100° C. for a period of time sufficient to substantially reduce the nitrosobenzene and subsequently reacting the resulting product mixture with from about 1 to about 3 mole equivalents of carbon disulfide per mole or originally charged nitrosobenzene, at a temperature from about 200° C. to about 300° C., for a time sufficient to convert at least a portion of the reactants into 2-mercaptobenzothiazole.

DETAILED DESCRIPTION OF THE PREFERRED EMBODIMENTS

The nitrosobenzene required as an initial material in the process pursuant to the invention is easily obtained. It is produced by the catalytic hydrogenation of nitrobenzene. When, pursuant to a recent process (German patent application No. P 27 13 602) an aliphatic, cycloaliphatic, olefinic or aromatic hydrocarbon is used as the reducing agent, reduction will proceed with a high conversion rate and a high degree of selectivity.

It must be considered surprising, that nitrosobenzene can be transformed substantially quantitatively to 2-mercaptobenzothiazole with hydrogen sulfide and carbon disulfide. The reaction may be represented by a summation formula, as follows:

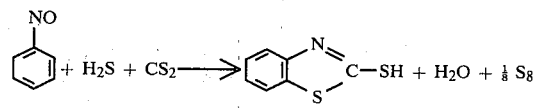

However, the reaction is in fact much more complicated and is composed of a great number of individual reactions partly taking place concurrently and partly taking place sequentially. At any rate, it can be stated with certainty that an initial quantitative reduction of the nitrosobenzene by hydrogen sulfide to aniline, which then reacts with carbon disulfide to 2-mercaptobenzothiazole in the known manner, is not possible. The main reaction product of nitrosobenzene and hydrogen sulfide is indeed aniline, which is formed with a yield of about 75%, but at least ten more reaction products with aromatic nitrogen groupings are also formed thereby. When this mixture of products is subsequently reacted with carbon disulfide, one nevertheless obtains an almost quantitative—based on the charged nitrosobenzene—yield of 2-mercaptobenzothiazole, thus a much higher yield than would correspond to the aniline content of the reaction mixture. It follows therefore, that, surprisingly, the other reaction products are also transformed into 2-mercaptobenzothiazole. Therefore, when the nitrosobenzene is being reacted with hydrogen sulfide and carbon disulfide at the same time, in keeping with the invention, the reaction will produce the desired 2-mercaptobenzothiazole with high selectivity and yield.

As already stated above, the stoichiometric ratio of the reactants, nitrosobenzene, carbon disulfide and hydrogen sulfide, is 1:1:1. Excesses of hydrogen sulfide and carbon disulfide exert a favorable influence on the selectivity of the reaction to 2-mercaptobenzothiazole and on the purity of the latter. Therefore, 1.5 to 4 mols hydrogen sulfide and 1 to 3 mols of carbon disulfide are charged per mol of nitrosobenzene. Preference is given to a molar ratio of nitrosobenzene: hydrogen sulfide: carbon disulfide of about 1:1.8 to 3:1.2 to 1.5. Large excesses of hydrogen sulfide and carbon disulfide do not have an adverse effect on the reaction, but are not advisable for economic reasons.

The reaction pressure is not critical and is determined by the partial pressures of the participants in the reaction at the selected conversion temperatures. As in all reactions determined by mass transfer, the reaction time in the present case as well is pressure-dependent and, for example, by increasing the hydrogen sulfide pressure, it is possible to attain shorter reaction times. In general, however, reaction pressures which are too high will result in difficulties with the equipment and require greater investments, so that part of the obtained advantage is lost again. It is possible to work within a wide range of pressures, beginning with about 1 bar, up to about 150 bar, but preference is given to the range from about 5 to about 100 bar, in particular about 15 to about 65 bar.

The following may be said with respect to the reaction temperature: Vigorous reduction of the nitrosobenzene already starts at room temperature and its progress is strongly exothermic. The cyclization reactions start at 200° C., and at 220° C. and above they proceed quickly and practically quantitatively. This results in the following for the execution of the process pursuant to the invention:

In the mode of operation in which the nitrosobenzene is first reduced with hydrogen sulfide, the reaction is first carried out at temperatures in the range from about 20° to about 100° C., until the nitrosobenzene is substantially reduced. Since the reaction proceeds vigorously, the hydrogen sulfide must be supplied slowly and carefully in order to avoid spontaneous decomposition of the nitrosobenzene. Suitably, the reduction is carried out in the presence of an inert solvent. Lower aliphatic alcohols with about 1 to about 12 carbon atoms are suitable for this purpose, such as methanol, ethanol, propanol, isopropanol, butanol, isobutanol, amyl alcohols and isoamyl alcohols, as well as cyclohexane and hydrocarbons, such ligroin and kerosene fractions, aromatic and alkylaromatic compounds, such as benzene, toluene, the xylenes, ethyl benzene and cumene. Preferred solvents are benzene, toluene, the xylenes, cyclohexane, methanol, ethanol and isopropanol. The resulting reaction mixture is then heated, and temperatures of at least about 200° C. must be used. Since at about 200° C. cyclization of the reaction products with carbon disulfide to 2-mercaptobenzothiazole still proceeds relatively slowly, it is advisable to use reaction temperatures of at least about 220° C. Preferred reaction temperatures for cyclization are about 220° to about 265° C. Higher temperatures, up to about 350° C., can also be used for cyclization, but they are not economically feasible and are not otherwise advisable, because at such high reaction temperatures there will be losses in yield due to continued reaction of the 2-mercaptobenzothiazole.

No general statement may be made concerning the reaction time, since it depends upon a number of factors, such as the stoichiometric ratio of the reaction components, the reaction pressure, reaction temperature and, in particular, the stirring velocity. The end of the reaction can easily be determined from the fact that the reaction pressure remains constant. This is so, because first the pressure drops because of the consumption of hydrogen sulfide, and then rises again, from 200° C. on, due to the starting of the cyclization reaction and the re-formation of hydrogen sulfide connected therewith. After complete conversion of the nitrosobenzene to 2-mercaptobenzothiazole the pressure finally remains constant and is only a function of the temperature.

The process pursuant to the present invention is exceptionally well suited for the industrial preparation of 2-mercaptobenzothiazole and may be performed discontinuously, as well as continuously. Compared with the known industrial processes, the process has several advantages. It is distinguished by the fact that no catalysts are needed, but shorter reaction times are nevertheless attained. Beyond that, one obtains quantitative conversions and substantially higher yields than with the known processes. In an economic and processing-technological respect, it is especially advantageous that no additional auxiliary chemicals and no undesirable and unusable waste or by-products result, and that the process may be carried out at relatively low pressures. The sulfur accumulating as a by-product in the process can be utilized in the production of carbon disulfide, while the required hydrogen sulfide is again obtained as a by-product in in carbon disulfide production. And finally it must also be pointed out that, in the process pursuant to the present invention, 2-mercaptobenzothiazole is obtained with high purity, so that its purification is unnecessary. Thus, the auxiliary chemicals required in the known process are not needed and the flows of waste resulting therefrom do not occur.

Examples 1 to 8

Nitrosobenzene in solid form is filled into a No. 316 stainless steel autoclave equipped with gas supply tube, flow breaker, manometer, stirring device and gas discharge valve, and subsequently the reaction vessel is closed and the appropriate quantity of carbon disulfide supplied via a steel capillary. After that, the desired quantity of hydrogen sulfide is forced into the reaction vessel at room temperature, which is accompanied by a distinct, exothermic reaction. The reaction mixture is quickly heated to 240° to 250° C. with vigorous stirring. After termination of the reaction (constant hydrogen sulfide pressure), stirring is continued for 15 min. at 245° C. and the reaction vessel is emptied. For this purpose the reaction mixture is either withdrawn at 180° C. in the form of a melt via an immersion tube, or the content of the reactor is cooled to room temperature, taken up in methanol and finally the formed sulfur separated from the 2-mercaptobenzothiazole by filtration. Pure 2-mercaptobenzothiazole in crystalline form is left after removal of the methanol. Additional purification of the 2-mercaptobenzothiazole (e.g. by reprecipitation via its alkali salts) is not necessary, since there are no polymeric products. The purity of the compound is confirmed by acidimetric and argentometric titration, as well as analyses by means of liquid chromatography. The Table shows the experimental conditions, the conversion rates, as well as the yields based on 2-mercaptobenzothiazole and based on sulfur.

Example 9

10 g (93 mol) of nitrosobenzene are filled into the equipment described for Examples 1 to 8 and 5.2 g (150 mmol) of hydrogen sulfide are gradually added thereto with stirring. The reaction temperature is 80° C., the pressure is 3 bar and the reaction time is one hour. The conversion rate based on nitrosobenzene is 100%. The reaction mixture contained 77.5% of the theoretical amount of aniline, as well additional nitrogen-functional compounds.

The reaction mixture obtained in this manner is then within 30 minutes heated to 245° C. with 6.6 g (110 mmol) of carbon disulfide and then left at this temperature for an additional 30 minutes. Based on the entire process, the conversion rate is 100%, the yield of sulfur is 99.5% and that of 2-mercaptobenzothiazole is 98.5% of theoretical. Melting point: 179°–181° C.

Example 10

10 g (93 mmol) of nitrosobenzene and 50 ml of benzene are placed in the equipment described for Examples 1 to 8. Then, at 30° C., 5.2 g (150 mmol) of hydrogen sulfide is fed in and left at this temperature for one hour. The conversion rate, based on the nitrosobenzene, is 100%, the yield of sulfur is 75.8% and the yield of aniline is 74.7%.

Subsequently, 50 g (827 mmol) of carbon disulfide are added to the reaction mixture which, in addition to aniline, also contains other nitrogen-functional compounds. It is then heated to 250° C. in the course of 30 minutes. The pressure is 28 bar and the reaction mixture is processed after another 30 minutes reaction time. Based on the entire reaction, the yield of 2-mercaptobenzothiazole is 88.8% of theoretical. Melting point: 180°–181.5° C.

What we claim is:

1. A process for the preparation of 2-mercaptobenzothiazole comprising heating a reaction mixture comprising nitrosobenzene, hydrogen sulfide and carbon disulfide in a molar ratio of about 1:1.5 to 4:1 to 3, respectively, to a temperature from about 200° to about 300° C., for a time sufficient to convert at least a portion of the reactants into 2-mercaptobenzothiazole.

2. A process for the preparation of 2-mercaptobenzothiazole comprising first reacting nitrosobenzene with hydrogen sulfide in a molar ratio of about 1:1.5 to 4, at a temperature from about 20° to about 100° C. for a period of time sufficient to substantially reduce the nitrosobenzene and subsequently reacting the resulting product mixture with from about 1 to about 3 mole equivalents of carbon disulfide per mole of originally charged nitrosobenzene, at a temperature from about 200° C. to about 300° C.

3. The process of claim 1 wherein the heating is performed at an elevated pressure.

4. The process of claim 2 wherein the heating is performed at an elevated pressure.

5. The process of claims 1, 2, 3, or 4 wherein the molar ratio of nitrosobenzene: hydrogen sulfide: carbon disulfide charged during the reaction is about 1:1.8 to 3:1.2 to 1.5.

6. The process of claim 3 or 4 wherein the reaction pressure at the final temperature is from about 15 to about 65 bar.

7. The process of claim 5 wherein the reaction pressure at the final temperature is about 15 to about 65 bar.

8. The process of claim 2 or 4 wherein the reaction of the nitrosobenzene with hydrogen sulfide is performed in the presence of an inert solvent.

9. The process of claim 8 wherein the inert solvent is selected from the group consisting of benzene, toluene, xylenes, cyclohexane, methanol, ethanol, and isopropanol.

10. The process of claim 9 wherein the molar ratio of nitrosobenzene: hydrogen sulfide: carbon disulfide charged during the reaction is about 1:1.8 to 3:1.2 to 1.5.

11. The process of claim 10 wherein the reaction pressure at the final temperature is from about 15 to about 65 bar.

TABLE

| Example | Nitrosobenzene g | mmol | Carbon Disulfide g | mmol | Hydrogen Sulfide g | mmol | Temp. °C. | Heatup Time hrs. | Total Time hrs. | Pres. Bar | Conv. Rate % | Mercaptobenzothiazole % | Sulfur % |
|---|---|---|---|---|---|---|---|---|---|---|---|---|---|
| 1 | 5.35 | 50 | 6.6 | 110 | 5.9 | 173 | 245 | 0.5 | 1.5 | 65 | 100 | 96.4 | 100 |
| 2 | 5.35 | 50 | 4.0 | 66 | 5.2 | 150 | 250 | 1 | 2 | 52 | 99.5 | 95.8 | 99.2 |
| 3 | 11.7 | 100 | 10.0 | 166 | 6.2 | 180 | 240 | 0.5 | 1.5 | 36 | 100 | 94.6 | 98.5 |
| 4 | 7.7 | 70 | 5.0 | 83 | 5.2 | 150 | 255 | 0.5 | 1.5 | 42 | 100 | 98.7 | 100 |
| 5 | 53.5 | 500 | 50.0 | 827 | 55.0 | 1600 | 245 | 1.5 | 3.5 | 85 | 100 | 99.2 | 100 |
| 6* | 5.35 | 50 | 6.6 | 110 | 5.2 | 150 | 200 | 0.5 | 1.5 | 41 | 100 | 44.5 | 96.5 |
| 7 | 5.35 | 50 | 6.6 | 110 | 5.2 | 150 | 220 | 0.5 | 1.5 | 61 | 100 | 85.7 | 99.5 |
| 8* | 5.35 | 50 | 6.6 | 110 | 5.2 | 150 | 320 | 0.5 | 1.5 | 98 | 100 | 87.5 | 94.5 |

*Comparative examples